US012611132B2

(12) United States Patent
Rapoport et al.

(10) Patent No.: US 12,611,132 B2
(45) Date of Patent: Apr. 28, 2026

(54) SYSTEMS AND METHODS FOR VISUALIZING BRAIN ACTIVITY IN REAL TIME AT HIGH SPATIAL AND TEMPORAL RESOLUTION

(71) Applicant: PRECISION NEUROSCIENCE CORPORATION, New York, NY (US)

(72) Inventors: Benjamin I. Rapoport, New York, NY (US); Mark Hettick, New York, NY (US); Elton Ho, New York, NY (US); Adam J. Poole, New York, NY (US); Manuel Monge, New York, NY (US); Demetrios Papageorgiou, New York, NY (US); Daniel Trietsch, New York, NY (US); Kyle Reed, New York, NY (US); Mark Murphy, New York, NY (US); Stephanie Rider, New York, NY (US); Craig H. Mermel, New York, NY (US)

(73) Assignee: PRECISION NEUROSCIENCE CORPORATION, New York, NY (US)

( * ) Notice: Subject to any disclaimer, the term of this patent is extended or adjusted under 35 U.S.C. 154(b) by 0 days.

(21) Appl. No.: 18/908,314

(22) Filed: Oct. 7, 2024

(65) Prior Publication Data

US 2025/0114024 A1     Apr. 10, 2025

Related U.S. Application Data

(60) Provisional application No. 63/542,926, filed on Oct. 6, 2023.

(51) Int. Cl.
*A61B 5/05*        (2021.01)
*A61B 5/00*        (2006.01)
*A61B 5/293*       (2021.01)

(52) U.S. Cl.
CPC ............ *A61B 5/293* (2021.01); *A61B 5/6847* (2013.01); *A61B 5/742* (2013.01);
(Continued)

(58) Field of Classification Search
CPC ......... A61B 5/374; A61B 5/369; A61B 5/291; A61B 5/0006; A61B 5/4035; A61B 5/24;
(Continued)

(56) References Cited

U.S. PATENT DOCUMENTS 5,709,689 A     1/1998  Ferrante et al.
5,910,282 A     6/1999  Grozdanovski et al.
(Continued)

FOREIGN PATENT DOCUMENTS

AU      2020428944 A1      9/2022
AU      2024203319 A1      6/2024
(Continued)

OTHER PUBLICATIONS

Haufe et al. "Elucidating relations between fMRI, ECoG and EEG through a common natural stimulus" Publication bioR$_\chi$iv. Oct. 22, 2017. (Year: 2017).*
(Continued)

*Primary Examiner* — Joseph A Stoklosa
*Assistant Examiner* — Brian M Antiskay
(74) *Attorney, Agent, or Firm* — DLA Piper LLP US

(57)          ABSTRACT

A device and system for real-time visualization of the electrophysiologic activity of a brain, particularly at the cortical surface. The neural device can acquire, process, and display high-spatiotemporal-resolution electrophysiologic data in real-time across entire electrode arrays spanning many thousands of electrodes over identified anatomic regions. The system is compatible with thin-film cortical surface electrodes that record from neural tissues without damaging those tissues. The system can be used to guide
(Continued)

diagnostic and therapeutic actions with high precision, and also provides the basis for a brain-computer interface.

15 Claims, 11 Drawing Sheets

(52) U.S. Cl.
CPC . *A61B 2560/045* (2013.01); *A61B 2560/0468* (2013.01); *A61B 2562/046* (2013.01); *A61B 2562/164* (2013.01)

(58) Field of Classification Search
CPC ............... A61B 5/6814; A61B 5/0031; A61B 2018/00839; A61B 5/283; A61B 5/282; A61B 5/372; A61B 5/4821; A61B 5/388; A61B 5/0002; A61B 5/0017; A61B 2562/227; A61B 5/076; A61B 5/287; A61B 5/31; A61B 5/37; A61B 5/4041; A61B 5/4064; A61B 5/4088; A61N 1/36082; A61N 1/375; A61N 1/0529; A61N 1/3605; A61N 1/0531
USPC ........ 600/372–374, 377–378, 393, 544–545; 607/115–123
See application file for complete search history.

(56) References Cited

U.S. PATENT DOCUMENTS

| | | | |
|---|---|---|---|
| 6,831,991 | B2 | 12/2004 | Fridrich et al. |
| 7,389,144 | B1 | 6/2008 | Osorio et al. |
| 7,818,061 | B1 | 10/2010 | Palmer |
| 7,925,350 | B1 | 4/2011 | Palmer |
| 8,156,568 | B2 | 4/2012 | Gaitas et al. |
| 8,170,670 | B2 | 5/2012 | Stubbs et al. |
| 8,515,538 | B1 | 8/2013 | Osorio et al. |
| 8,516,568 | B2 | 8/2013 | Cohen |
| 8,546,568 | B2 | 10/2013 | Inouye et al. |
| 8,634,918 | B2 | 1/2014 | Chambers |
| 9,314,618 | B2 | 4/2016 | Imran et al. |
| 9,549,704 | B1 | 1/2017 | Buerger et al. |
| 10,135,849 | B2 | 11/2018 | Jha et al. |
| 10,265,081 | B2 | 4/2019 | Kennedy et al. |
| 10,363,420 | B2 | 7/2019 | Fried et al. |
| 11,013,923 | B1 | 5/2021 | Eubanks |
| 11,185,684 | B2 | 11/2021 | Cadwell |
| 11,640,204 | B2 | 5/2023 | Shenoy et al. |
| 12,008,987 | B2 | 6/2024 | Stavisky et al. |
| 2001/0054758 | A1 | 12/2001 | Isaak |
| 2003/0057506 | A1 | 3/2003 | Li et al. |
| 2005/0228421 | A1 | 10/2005 | Bilenski et al. |
| 2005/0261934 | A1 | 11/2005 | Thompson |
| 2006/0015153 | A1 | 1/2006 | Gliner et al. |
| 2006/0106431 | A1 | 5/2006 | Wyler et al. |
| 2006/0253163 | A1 | 11/2006 | Stubbs et al. |
| 2007/0005691 | A1 | 1/2007 | Pushparaj |
| 2007/0282398 | A1 | 12/2007 | Healy et al. |
| 2009/0082829 | A1 | 3/2009 | Panken et al. |
| 2009/0088763 | A1 | 4/2009 | Aram et al. |
| 2009/0132061 | A1 | 5/2009 | Stubbs et al. |
| 2009/0312817 | A1 | 12/2009 | Hogle et al. |
| 2011/0093052 | A1 | 4/2011 | Anderson et al. |
| 2011/0245835 | A1 | 10/2011 | Dodds et al. |
| 2012/0139269 | A1 | 6/2012 | Kouzuma |
| 2012/0277834 | A1 | 11/2012 | Mercanzini et al. |
| 2012/0302959 | A1 | 11/2012 | Fielder et al. |
| 2013/0014982 | A1 | 1/2013 | Segawa et al. |
| 2013/0144362 | A1 | 6/2013 | Lee |
| 2013/0144365 | A1* | 6/2013 | Kipke .................. A61B 5/4064 607/148 |
| 2013/0331856 | A1 | 12/2013 | Sage |
| 2014/0051960 | A1 | 2/2014 | Badower et al. |
| 2014/0081127 | A1 | 3/2014 | Patil et al. |

| | | | |
|---|---|---|---|
| 2014/0100586 | A1 | 4/2014 | Pianca et al. |
| 2014/0194944 | A1 | 7/2014 | Romanelli et al. |
| 2015/0111930 | A1 | 4/2015 | Aung-Din |
| 2015/0151114 | A1 | 6/2015 | Black et al. |
| 2015/0265180 | A1 | 9/2015 | Venkatesan et al. |
| 2015/0367122 | A1* | 12/2015 | Morshed ............... A61B 5/296 600/372 |
| 2016/0007874 | A1* | 1/2016 | Ma ...................... A61B 5/6868 600/377 |
| 2016/0120457 | A1 | 5/2016 | Wu et al. |
| 2016/0174863 | A1 | 6/2016 | Foerster et al. |
| 2016/0331994 | A1 | 11/2016 | Smith et al. |
| 2017/0100580 | A1 | 4/2017 | Olson |
| 2017/0108926 | A1 | 4/2017 | Moon et al. |
| 2017/0113046 | A1 | 4/2017 | Fried et al. |
| 2017/0224980 | A1 | 8/2017 | Grasso et al. |
| 2017/0235663 | A1 | 8/2017 | Kattepur et al. |
| 2017/0246452 | A1 | 8/2017 | Liu et al. |
| 2017/0259072 | A1 | 9/2017 | Newham et al. |
| 2018/0078767 | A1 | 3/2018 | Rapoport et al. |
| 2018/0236221 | A1 | 8/2018 | Opie et al. |
| 2018/0332009 | A1 | 11/2018 | Lange |
| 2019/0110754 | A1 | 4/2019 | Rao et al. |
| 2019/0134396 | A1 | 5/2019 | Toth et al. |
| 2019/0150774 | A1 | 5/2019 | Brinkmann et al. |
| 2019/0333505 | A1 | 10/2019 | Stavisky et al. |
| 2020/0061374 | A1 | 2/2020 | Mitchell |
| 2020/0069427 | A1 | 3/2020 | Swennen et al. |
| 2020/0078586 | A1 | 3/2020 | Wijseundara et al. |
| 2020/0155828 | A1* | 5/2020 | Shepard ................. A61B 5/293 |
| 2020/0206503 | A1 | 7/2020 | Ganzer et al. |
| 2020/0215318 | A1 | 7/2020 | Fielder et al. |
| 2020/0222010 | A1* | 7/2020 | Howard ................... G06N 5/02 |
| 2020/0297228 | A1 | 9/2020 | Crawford et al. |
| 2020/0310442 | A1 | 10/2020 | Halder et al. |
| 2020/0337579 | A1 | 10/2020 | Auerbach et al. |
| 2020/0364539 | A1 | 11/2020 | Anisimov et al. |
| 2021/0033559 | A1 | 2/2021 | Panat et al. |
| 2021/0034906 | A1 | 2/2021 | Van Welzen et al. |
| 2021/0085988 | A1 | 3/2021 | Nin et al. |
| 2021/0186450 | A1 | 6/2021 | Vancamberg et al. |
| 2021/0213279 | A1 | 7/2021 | Rapoport et al. |
| 2021/0252289 | A1 | 8/2021 | Esteller |
| 2021/0267523 | A1 | 9/2021 | Donoghue et al. |
| 2021/0267526 | A1 | 9/2021 | Bishay et al. |
| 2021/0268265 | A1 | 9/2021 | Eder et al. |
| 2021/0272687 | A1 | 9/2021 | Klopfenstein et al. |
| 2021/0275807 | A1 | 9/2021 | Bouton |
| 2021/0280309 | A1 | 9/2021 | Klopfenstein et al. |
| 2021/0353439 | A1 | 11/2021 | Norman et al. |
| 2022/0005465 | A1 | 1/2022 | Prabhavalkar et al. |
| 2022/0117511 | A1* | 4/2022 | Shor ................... A61B 5/6852 |
| 2022/0175320 | A1 | 6/2022 | Shah et al. |
| 2022/0184403 | A1 | 6/2022 | Chouinard et al. |
| 2022/0208173 | A1 | 6/2022 | Chang et al. |
| 2022/0211312 | A1 | 7/2022 | Brinkmann et al. |
| 2022/0218264 | A1 | 7/2022 | Brunner et al. |
| 2022/0240833 | A1 | 8/2022 | Oxley |
| 2022/0301563 | A1 | 9/2022 | Chang et al. |
| 2022/0330868 | A1 | 10/2022 | Crawford et al. |
| 2022/0370805 | A1 | 11/2022 | Cogan et al. |
| 2022/0379117 | A1 | 12/2022 | Spector |
| 2022/0413612 | A1 | 12/2022 | Gribetz |
| 2023/0059718 | A1 | 2/2023 | Hor-Lao et al. |
| 2023/0062326 | A1 | 3/2023 | Colachis et al. |
| 2023/0075205 | A1* | 3/2023 | Moran ............... A61N 1/37211 |
| 2023/0111217 | A1 | 4/2023 | Weiss |
| 2023/0113727 | A1 | 4/2023 | Van Der Zalm et al. |
| 2023/0210427 | A1 | 7/2023 | Rapoport et al. |
| 2023/0253104 | A1 | 8/2023 | Serruya |
| 2023/0271007 | A1 | 8/2023 | Ganzer et al. |
| 2023/0320417 | A1 | 10/2023 | Renner et al. |
| 2023/0389851 | A1 | 12/2023 | Tal et al. |
| 2023/0414947 | A1 | 12/2023 | Esteller |
| 2024/0008788 | A1 | 1/2024 | Crawford et al. |
| 2024/0029717 | A1 | 1/2024 | Jain et al. |
| 2024/0115178 | A1 | 4/2024 | Rapoport et al. |
| 2024/0139512 | A1 | 5/2024 | Schulhauser et al. |
| 2024/0374893 | A1 | 11/2024 | Robinson et al. |

(56) References Cited

U.S. PATENT DOCUMENTS

| | | | |
|---|---|---|---|
| 2024/0399152 A1 | 12/2024 | Powell et al. | |
| 2024/0412030 A1 | 12/2024 | Guinn et al. | |
| 2025/0010070 A1 | 1/2025 | Ganzer et al. | |
| 2025/0213159 A1 | 7/2025 | Crawford et al. | |

FOREIGN PATENT DOCUMENTS

| CN | 110876652 | A | 3/2020 |
|---|---|---|---|
| KR | 20200074951 | A | 6/2020 |
| WO | 2008052166 | A2 | 5/2008 |
| WO | 2012143850 | A1 | 10/2012 |
| WO | 2014047152 | A1 | 3/2014 |
| WO | 2015191628 | A1 | 12/2015 |
| WO | 2015195553 | A1 | 12/2015 |
| WO | 2017160627 | A2 | 9/2017 |
| WO | 2017196971 | A1 | 11/2017 |
| WO | 2019079475 | A1 | 4/2019 |
| WO | 2019152648 | A1 | 8/2019 |
| WO | 2019211314 | A1 | 11/2019 |
| WO | 2020008016 | A1 | 1/2020 |
| WO | 2020008017 | A1 | 1/2020 |
| WO | 2020142384 | A1 | 7/2020 |
| WO | 2020219371 | A1 | 10/2020 |
| WO | 2021021714 | A1 | 2/2021 |
| WO | 2021055682 | A1 | 3/2021 |
| WO | 2021162795 | A1 | 8/2021 |
| WO | 2021174061 | A1 | 9/2021 |
| WO | 2022011260 | A1 | 1/2022 |
| WO | 2022126059 | A1 | 6/2022 |
| WO | 2022251151 | A1 | 12/2022 |
| WO | 2024254360 | A1 | 12/2024 |

OTHER PUBLICATIONS

Tchoe et al. "Human Brain Mapping with Multi-Thousand Channel PtNR Grids Resolves Spatiotemporal Dynamics" Sci Transl Med. Jan. 19, 2022; 14(628). (Year: 2022).*

Bridges et al. "MEA Viewer: A high-performance interactive application for visualizing electrophysiological data" Feb. 9, 2018. (Year: 2018).*

Matsushita et al. A Fully Implantable Wireless ECoG 128-Channel Recording Device for Human Brain-Machine Interfaces: W-HERBS. Front. Neurosci. 12:511. Jul. 30, 2018. (Year: 2018).*

Camara C., et al., "Security and Privacy Issues in Implantable Medical Devices: A Comprehensive Survey," Journal of Biomedical Informatics, Jun. 11, 2015, vol. 55, 45 pages.

Hettick M., et al., "The Layer 7 Cortical Interface: a Scalable and Minimally Invasive Brain-computer Interface Platform," bioRxiv, Jan. 30, 2024, 42 pages.

International Preliminary Report on Patentability for Application No. PCT/US2022/78130, mailed on Apr. 25, 2024, 8 Pages.

International Preliminary Report on Patentability for the Application No. PCT/US2022/82619, mailed on Jul. 11, 2024, 9 pages.

International Preliminary Report on Patentability for the Application No. PCT/US2023/063894, mailed Sep. 19, 2024, 12 pages.

International Search Report and Written Opinion for Application No. PCT/US2022/078130, mailed on Feb. 16, 2023, 11 pages.

International Search Report and Written Opinion for Application No. PCT/US2022/082619, mailed on Jun. 2, 2023, 16 pages.

International Search Report and Written Opinion for Application No. PCT/US2023/035620 mailed on Feb. 15, 2024, 14 pages.

International Search Report and Written Opinion for Application No. PCT/US2023/035623, mailed on Feb. 8, 2024, 10 pages.

International Search Report and Written Opinion for Application No. PCT/US2023/035624, mailed on Feb. 26, 2024, 15 pages.

International Search Report and Written Opinion for Application No. PCT/US2023/035625, mailed on Feb. 26, 2024, 13 pages.

International Search Report and Written Opinion for Application No. PCT/US2023/035627, mailed on Feb. 9, 2024, 13 pages.

International Search Report and Written Opinion for Application No. PCT/US2023/077626, mailed on Feb. 28, 2024, 12 pages.

International Search Report and Written Opinion for Application No. PCT/US2024/017647, mailed on Jun. 6, 2024, 13 pages.

International Search Report and Written Opinion for Application No. PCT/US2024/028423, mailed on Jul. 18, 2024, 13 pages.

International Search Report and Written Opinion for the application No. PCT/US2023/063894, mailed on Sep. 29, 2023, 14 pages.

Kim T., et al., "Spatiotemporal Compression for Efficient Storage and Transmission of High-Resolution Electrocorticography Data," Annual International Conference of the IEEE Engineering in Medicine and Biology Society, Aug. 28, 2012, pp. 1012-1015.

Liu X., et al., "An Energy-Efficient Compressed Sensing-Based Encryption Scheme for Wireless Neural Recording," IEEE Journal on Emerging and Selected Topics in Circuits and Systems, Jun. 2021, vol. 11, No. 2, pp. 405-414.

Office Action for Canadian Patent Application No. 3241544, mailed Jul. 25, 2024, 3 pages.

Sorrell E., et al., "Brain-machine Interfaces: Closed-loop Control in an Adaptive System," Annual Review of Control, Robotics, and Autonomous Systems, Jan. 29, 2021, vol. 4, pp. 167-189.

Wang N.X.R., et al., "Unsupervised Decoding of Long-Term, Naturalistic Human Neural Recordings with Automated Video and Audio Annotations," Frontiers in Human Neuroscience, Apr. 21, 2016, vol. 10, No. 165, 13 pages.

Alim S.A., et al., "Some Commonly Used Speech Feature Extraction Algorithms," IntechOpen, 2018, vol. 1, 18 pages.

Anumanchipalli G.K., et al., "Speech Synthesis from Neural Decoding of Spoken Sentences," Nature, Apr. 2019, vol. 568, No. 7753, pp. 493-498.

Collobert R., et al., "A Fully Differentiable Beam Search Decoder," A preprint, Feb. 19, 2019, 11 pages.

Defossez A., et al., "Decoding Speech Perception from Non-invasive Brain Recordings," Nature Machine Intelligence, Oct. 5, 2023, vol. 5, pp. 1097-1107.

Duraivel S., et al., "High-resolution Neural Recordings Improve the Accuracy of Speech Decoding," Nature Communications, Nov. 6, 2023, vol. 14, No. 6938, 16 pages.

Inclusive Technology., "Inclusive Eyegaze Education with Mygaze Eye Tracker—Discontinued," Spectronics, Feb. 25, 2025, 8 pages, Retrieved from the Internet: URL: https://www.spectronics.com.au/product/inclusive-eyegaze-education-with-mygaze-eye-tracker#mygaze.

International Search Report and Written Opinion for Application No. PCT/US2024/043449, mailed on Nov. 15, 2024, 16 pages.

International Search Report and Written Opinion for Application No. PCT/US2025/011619, mailed on Mar. 27, 2025, 13 Pages.

Meta., "AI Speech Research Voicebox: Text-guided Multilingual Universal Speech Generation at Scale," Voicebox, Research by Meta AI, 2023, Retrieved on Feb. 25, 2025, 8 pages, Retrieved from the Internet: URL: https://thevoicebox.metademolab.com/.

Biederman W., et al., "A Fully-Integrated, Miniaturized (0.125 $mm^2$) 10.5 $\mu W$ Wireless Neural Sensor," IEEE Journal of Solid-state Circuits, 2013, vol. 48, No. 4, pp. 960-970.

Chen Z.S., "Emerging Brain-to-content Technologies from Generative Al and Deep Representation Learning In the Spotlight)," IEEE Signal Processing Magazine, Nov. 2024, vol. 41, No. 6, pp. 94-104.

Coelho K., et al., "Cryptographic Algorithms in Wearable Communications: An Empirical Analysis," IEEE Communications Letters, 2019, vol. 23, No. 11, pp. 1931-1934.

Examination Report No. 1 for Australian Patent Application No. 2023230897 dated Jun. 26, 2025, 10 pages.

Ghoreishizadeh S.S., et al., "A Lightweight Cryptographic System for Implantable Biosensors," Proceedings of 2014 IEEE Biomedical Circuits and Systems Conference (BioCAS), 2014, pp. 472-475.

Hinterberger T., et al., "Voluntary Brain Regulation and Communication with Electrocorticogram Signals," Epilepsy and Behavior, Aug. 1, 2008, vol. 13, No. 2, pp. 300-306.

International Preliminary Report on Patentability for the Application No. PCT/US2023/035620, mailed May 1, 2025, 9 pages.

International Preliminary Report on Patentability for the Application No. PCT/US2023/035623, mailed May 1, 2025, 9 pages.

(56) References Cited

OTHER PUBLICATIONS

International Preliminary Report on Patentability for the Application No. PCT/US2023/035624, mailed May 1, 2025, 9 pages.
International Preliminary Report on Patentability for the Application No. PCT/US2023/035625, mailed May 1, 2025, 7 pages.
International Preliminary Report on Patentability for the Application No. PCT/US2023/035627, mailed May 1, 2025, 8 pages.
International Search Report and Written Opinion for Application No. PCT/US2025/019165, mailed on Jun. 6, 2025, 18 pages.
Kim H., et al., "A Configurable and Low-Power Mixed Signal SoC for Portable ECG Monitoring Applications," IEEE Transactions on Biomedical Circuits and Systems, 2014, vol. 8, No. 2, pp. 257-267.
Schwemmer M.A., et al., "Meeting Brain-Computer Interface User Performance Expectations Using a Deep Neural Network Decoding Framework," Nature Medicine, Sep. 24, 2018, vol. 24, No. 11, pp. 1669-1676.
Yanagisawa T., et al., "Electrocorticographic Control of a Prosthetic Arm in Paralyzed Patients," Annals of Neurology, 2012, vol. 71, No. 3, pp. 353-361.
Beck C., et al., "Block Cipher Based Security for Severely Resource-Constrained Implantable Medical Devices," In Proceedings of the 4th International Symposium on Applied Sciences in Biomedical and Communication Technologies (ISABEL '11) Association for Computing Machinery, Oct. 26, 2011, No. 62, pp. 1-5.
Daemen J., et al., "AES Proposal: Rijndael," National Institute of Standards and Technology, 1999, 47 pages.
Judy M., et al., "A Nonlinear Signal-Specific ADC for Efficient Neural Recording," Biomedical Circuits and Systems Conference (BioCAS), 2010, pp. 17-20.
Kester Q.A., "A Cryptographic Image Encryption Technique for Facial-Blurring of Images," International Journal of Advanced Technology & Engineering Research, May 2013, vol. 3, No. 3, pp. 1-7.
Maji S., et al., "A Low-power Dual-Factor Authentication Unit for Secure Implantable Devices" IEEE Custom Integrated Circuits Conference (CICC), 2020, 10 pages, Retrieved from the Internet URL: https://arxiv.org/pdf/2004.13709.
Ogawa H., et al., "Rapid and Minimum Invasive Functional Brain Mapping by Real-time Visualization of High Gamma Activity During Awake Craniotomy," World Neurosurgery, Nov. 2014, 10 pages.
Pallud J., et al., Direct Electrical Bipolar Electrostimulation for Functional Cortical and Subcortical Cerebral Mapping in Awake Craniotomy. Practical Considerations, Neurochirurgie, Jun. 1, 2017, vol. 63, pp. 164-174.
Schneier B., "Description of a New Variable-Length Key, 64-Bit Block Cipher (Blowfish)," Fast Software Encryption, Cambridge Security Workshop Proceedings, Dec. 1993, pp. 191-204.
Third Party Prior Art Submission for U.S. Appl. No. 18/180,248, filed Aug. 12, 2025.
Thorpe C., et al., "A Coprime Blur Scheme for Data Security in Video Surveillance," In IEEE Transactions on Pattern Analysis and Machine Intelligence, 2013, vol. 35, No. 12, pp. 3066-3072.
Uy J., et al., "Stability of Maps of Human Motor Cortex Made with Transcranial Magnetic Stimulation," Brain Topography, Jun. 2002, vol. 14, No. 4, pp. 293-297.
Escabi M.A., et al., "A high-density, high-channel count, multiplexed muECOG array for auditory-cortex recordings" Journal of Neurophysiology, 2014, vol. 112, No. 6, pp. 1566-1583.
Office Action for Canadian Patent Application No. 3,245,576, mailed Oct. 14, 2025, 5 pages.
Rohaut B., et al., "Uncovering Consciousness in Unresponsive ICU Patients: Technical, Medical and Ethical Considerations," Critical Care, Mar. 9, 2019, vol. 23, No. 78, 9 pages, doi: 10.1186/s13054-019-2370-4.
"What are polymides?", UBE Corporation, accessed on Sep. 19, 2025, accessed at https://www.ube.com/ube/en/contents/chemical/ploymide/ploymide_column.html (Year: 2025).
Chidambaram S., et al., "Applications of Augmented Reality in the Neurosurgical Operating Room: A Systematic Review of the Literature," Journal of Clinical Neuroscience, 2021, vol. 91; pp. 43-61.
International Search Report and Written Opinion for Application No. PCT/US2025/026457, mailed on Aug. 18, 2025, 11 pages.

* cited by examiner

SYSTEMS AND METHODS FOR VISUALIZING BRAIN ACTIVITY IN REAL TIME AT HIGH SPATIAL AND TEMPORAL RESOLUTION

CROSS-REFERENCE TO RELATED APPLICATIONS

This application claims priority to U.S. Provisional Patent Application No. 63/542,926, titled SYSTEMS AND METH-ODS FOR VISUALIZING BRAIN ACTIVITY IN REAL TIME AT HIGH SPATIAL AND TEMPORAL RESOLU-TION, filed Oct. 6, 2023, which is hereby incorporated by reference herein in its entirety.

BACKGROUND

Brain-computer interfaces have shown promise as sys-tems for restoring, replacing, and augmenting lost or impaired neurological function in a variety of contexts, including paralysis from stroke and spinal cord injury, blindness, and some forms of cognitive impairment. Mul-tiple innovations over the past several decades have con-tributed to the potential of these neural interfaces, including advances in the areas of applied neuroscience and multi-channel electrophysiology, mathematical and computational approaches to neural decoding, power-efficient custom elec-tronics and the development of application-specific inte-grated circuits, as well as materials science and device packaging. Nevertheless, the practical impact of such sys-tems remains limited, with only a small number of patients worldwide having received highly customized interfaces through clinical trials.

High-bandwidth brain-computer interfaces are being developed to enable the bidirectional communication between the nervous system and external computer systems in order to assist, augment, or replace neurological function lost to disease or injury. A necessary capability of any brain-computer interface is the ability to accurately decode electrophysiologic signals recorded from populations of neurons, and to correlate such activity with one or more sensory stimuli or intended motor responses. For example, such a system may record activity from the primary motor cortex in a paralyzed human patient and attempt to predict the intended movement in a specific body part.

Furthermore, brain-penetrating microelectrode arrays have facilitated high-spatial-resolution recordings for brain-computer interfaces, but at the cost of invasiveness and tissue damage that scale with the number of implanted electrodes. In some applications, softer electrodes have been used in brain-penetrating microelectrode arrays; however, it is not yet clear whether such approaches offer a substantially different tradeoff as compared to conventional brain-pen-etrating electrodes. For this reason, non-penetrating cortical surface microelectrodes represent a potentially attractive alternative and form the basis of the system described here. In practice, electrocorticography (EcoG) has already facili-tated capture of high quality signals for effective use in brain-computer interfaces in several applications, including motor and speech neural prostheses. Higher-spatial-resolu-tion micro-electrocorticography (µEcoG) therefore repre-sents a promising combination of improved spatial resolu-tion, improved signal quality, and minimal invasiveness. Therefore, it would be highly beneficial for neural devices to make use of non-penetrating cortical interfaces based on micro-electrocorticography.

SUMMARY

The present disclosure is directed to systems and methods for real-time visualization of neural activity at the cortical surface of a patient in real-time via a neural interface.

In one embodiment, the present disclosure is directed to a neural device for real-time visualization of neural activity at a cortical surface of a patient, the neural device compris-ing: an electrode array comprising a plurality of electrodes, wherein the plurality of electrodes number at least about 500; wherein the electrode array records at a frequency from about 1 Hz to about 40 kHz; wherein a width of each of the plurality of electrodes is from about 10 µm to about 500 µm; wherein each of the plurality of electrodes is spaced from an adjacent electrode of the plurality of electrodes from about 200 µm to about 3,000 µm; and a transceiver coupled to the electrode array, the transceiver configured to transmit elec-trocortical data captured via the electrode array to an exter-nal device with a latency less than about 200 ms.

In one embodiment, the present disclosure is directed to a neural interface system for real-time visualization of neural activity at a cortical surface of a patient, the neural interface system comprising: a neural device comprising: an electrode array comprising a plurality of electrodes, wherein the plurality of electrodes number at least about 500, wherein the electrode array records at a frequency of up to about 30 kHz, wherein a width of each of the plurality of electrodes is from about 5 µm to about 50 µm, wherein each of the plurality of electrodes is spaced from an adjacent electrode of the plurality of electrodes by less than about 400 µm, and a transceiver coupled to the electrode array, the transceiver configured to transmit electrocortical data cap-tured via the electrode array to an external device with a latency less than about 200 ms; and an external device communicably coupled to the neural device via the trans-ceiver, the external device comprising a processor and a memory, the memory storing instructions that, when executed by the processor cause the external device to: receive the electrocortical data from the neural device, and render neural activity corresponding to the received electro-cortical data in real-time in correspondence with the anatomy of the cortical surface underlying the electrode array.

In some embodiments, low-latency data processing and rendering is facilitated by GPU-accelerated (graphics pro-cessing unit-accelerated) or GPU-optimized computation. In some embodiments, this GPU-accelerated or GPU-opti-mized computation is further facilitated by the pattern of electrode spacing across the two-dimensional electrode array.

In some embodiments, the plurality of electrodes com-prise electrodes that do not penetrate the cortical surface.

In some embodiments, the neural device is communicably coupled to an external device via the transceiver; and the electrocortical data can be visualized on the external device in real-time.

In some embodiments, the electrodes number 1,024, 2,048, 4,096, 8,192, or any other integer multiple of 1,024.

In some embodiments, the electrode array comprises a thin-film electrode array.

In some embodiments, the neural device comprises a flexible substrate on which the electrode array is disposed.

In some embodiments, the plurality of electrodes are spaced regularly.

In some embodiments, a rendering of the neural activity comprises at least one of spark-lines or colorized representations of voltage or spectral power associated with each of the plurality of electrodes.

In some embodiments, the electrode array comprises a micro-electrocorticography array based on electrodes micro-fabricated on a thin-film substrate.

In some embodiments, the electrode array comprises a micro-electrocorticography array based on metallic electrodes microfabricated on a polymer film substrate that is less than approximately 50 micrometers in thickness and capable of conforming in an atraumatic manner to the curved surface of the brain.

FIGURES

FIG. 4A-4C depict successive frames of an example real-time visualization of electrocortical activity overlaid on the cortical surface, in accordance with an embodiment of the present disclosure.

DETAILED DESCRIPTION

The electrical activity of the brain reflects important information related to healthy and disordered brain function. Information exchange within the brain occurs on multiple spatial and temporal scales, ranging from the sub-micron scale (e.g., individual cellular structures and processes) that occur at sub-millisecond speed to the centimeter scale (e.g., certain forms of oscillating electrical activity as well as aging processes) that occur over the span of years and decades. Many technologies have been developed to measure and display electrophysiologic activity of the brain. However, no existing technologies are able to record and display cortical surface activity in real-time, nondestructively, with resolutions in the hundreds of micrometers and over large portions of the surface of the brain.

The present disclosure is generally directed to surgical systems and methods for visualizing brain activity in real-time via neural interfaces. In particular, the disclosure is directed to systems and methods for fabricating neural interfaces having the requisite temporal resolution to record brain activity in real-time, processing of neural signals across large numbers of channels with the requisite latency to effectuate real-time visualization, and minimally invasive surgical techniques for deploying such neural interfaces for real-time visualization. The present disclosure further describes hardware and software that enables real-time visualization and computation of neural activity at high spatial and temporal resolution.

Being able to visualize cortical surface activity in real-time can be utilized in several different applications. For example, real-time visualization could be useful for diagnostic and therapeutic decision-making in neurological critical care (neuro-intensive care), as well as intraoperative decision-making during neurosurgery. In particular, real-time visualization of cortical surface activity could be used to identify which portions of the brain to ablate or remove in patients with brain tumors near eloquent (functional) areas, such as the areas related to language or motor function. Further, being able to visualize cortical surface activity in real-time could be used to determine the locations of seizure foci. Still further, real-time visualization of cortical surface activity could be used to determine whether a patient is suffering from seizures, micro-seizures, or cortical spreading depression, which are phenomena that can be treated medically and surgically when diagnosed properly and with precision.

Neural Device Systems

Figure 1:
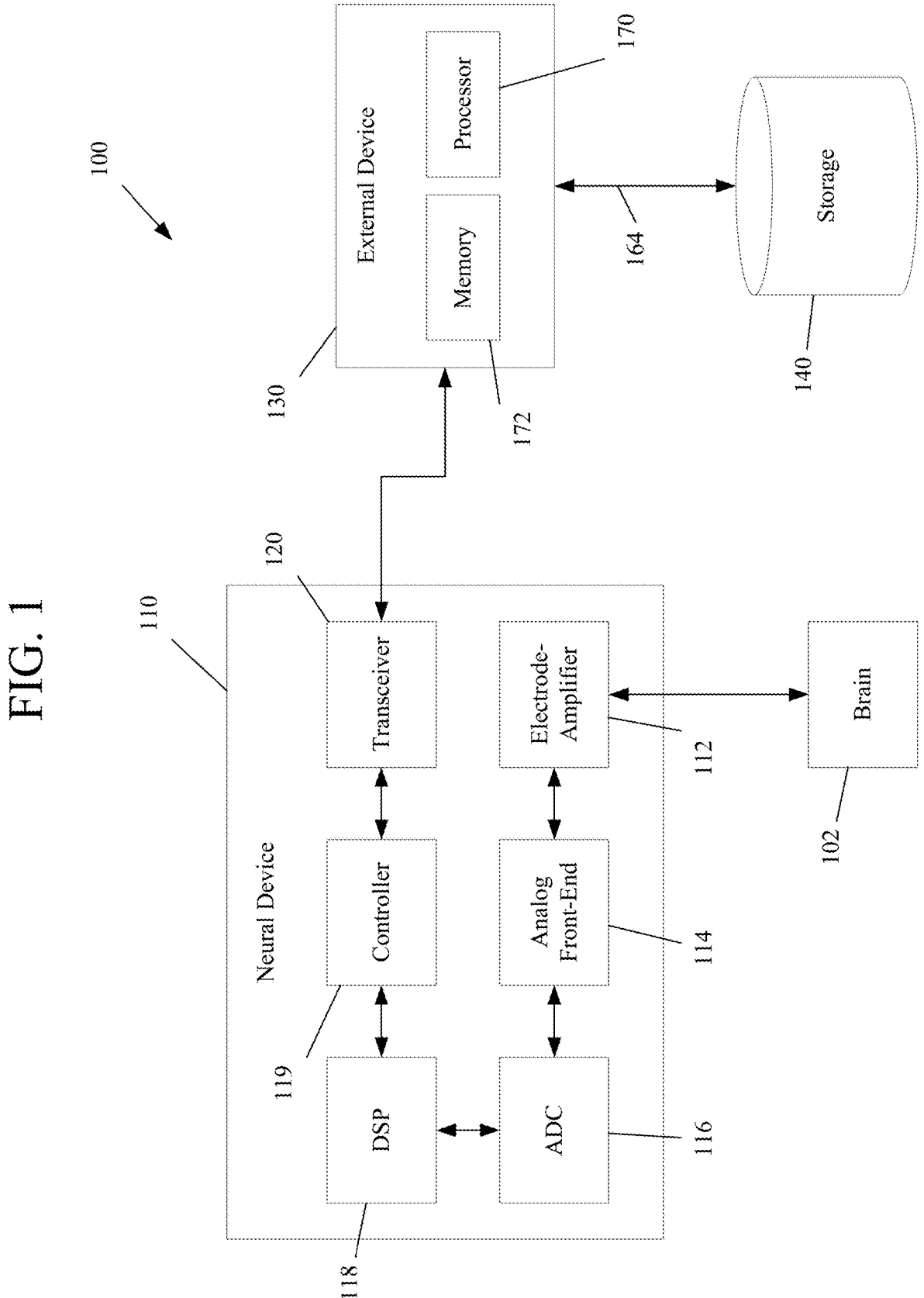
FIG. 1 depicts a block diagram of a secure neural device data transfer system, in accordance with an embodiment of the present disclosure.

Conventional neural devices typically include electrode arrays that penetrate a subject's brain in order to sense and/or stimulate the brain. However, the present disclosure is directed to the use of non-penetrating neural devices, i.e., neural devices having electrode arrays that do not penetrate the cortical surface. Such non-penetrating neural devices are minimally invasive and minimize the amount of impact on the subject's cortical tissue. Neural devices can sense and record brain activity, receive instructions for stimulating the subject's brain, and otherwise interact with a subject's brain as generally described herein. Referring now to FIG. 1, there is shown a diagram of an illustrative system 100 including a neural device 110 that is communicatively coupled to an external device 130. The external device 130 can include any device that the neural device 110 can be communicatively coupled, such as a computer system or mobile device (e.g., a tablet, a smartphone, a laptop, a desktop, a secure server, a smartwatch, a head-mounted virtual reality device, a head-mounted augmented reality device, or a smart inductive charger device). The external device 130 can include a processor 170 and a memory 172. In some embodiments, the external device 130 can include a server or a cloud-based computing system. In some embodiments, the external device 130 can further include or be communicatively coupled to storage 140. In one embodiment, the storage 140 can include a database stored on the external device 130. In another embodiment, the storage 140 can include a cloud computing system (e.g., Amazon Web Services or Azure).

The neural device 110 can include a range of electrical or electronic components. In the illustrated embodiment, the neural device 110 includes an electrode-amplifier stage 112, an analog front-end stage 114, an analog-to-digital converter (ADC) stage 116, a digital signal processing (DSP) stage 118, and a transceiver stage 120 that are communicatively coupled together. The electrode-amplifier stage 112 can include an electrode array, such as is described below, that is able to physically interface with the brain 102 of the subject in order to sense brain signals and/or apply electrical signals thereto. The analog front-end stage 114 can be configured, amplify signals that are sensed from or applied to the brain 102, perform conditioning of the sensed or applied analog signals, perform analog filtering, and so on. The front-end stage 114 can include, for example, one or more application-specific integrated circuits (ASICs) or other electronics. The ADC stage 116 can be configured to convert received analog signals to digital signals and/or convert received digital signals to an analog signal to be processed via the analog front-end stage 114 and then applied via the electrode-amplifier stage 112. The DSP stage 118 can be configured to perform various DSP techniques, including multiplexing of digital signals received via the electrode-amplifier stage 112 and/or from the external device 130. For example, the DSP stage 118 can be configured to convert instructions from the external device 130 to a corresponding digital signal. The transceiver stage 120 can be configured to transfer data from the neural device 110 to the external device 130 located outside of the body of the subject 102.

In some embodiments, the neural device 110 can further include a controller 119 that is configured to perform various functions, including compressing electrophysiologic data generated by the electrode array 180. In various embodiments, the controller 119 can include hardware, software, firmware, or various combinations thereof that are operable to execute the functions described below. In one embodiment, the controller 119 can include a processor (e.g., a microprocessor) executing instructions stored in a memory. In another embodiment, the controller 119 can include a field-programmable gate array (FPGA) or application-specific integrated circuit (ASIC).

In various embodiments, the stages of the neural device 110 can provide unidirectional or bidirectional communications (as indicated in FIG. 1) by and between the neural device 110 and the external device 130. In various embodiments, one or more of the stages can operate in a serial or parallel manner with other stages of the system 100. It can further be noted that the depicted architecture for the system 100 is simply intended for illustrative purposes and that the system 100 can be arranged differently (i.e., components or stages can be connected in different manners) or include additional components or stages.

Figure 2:
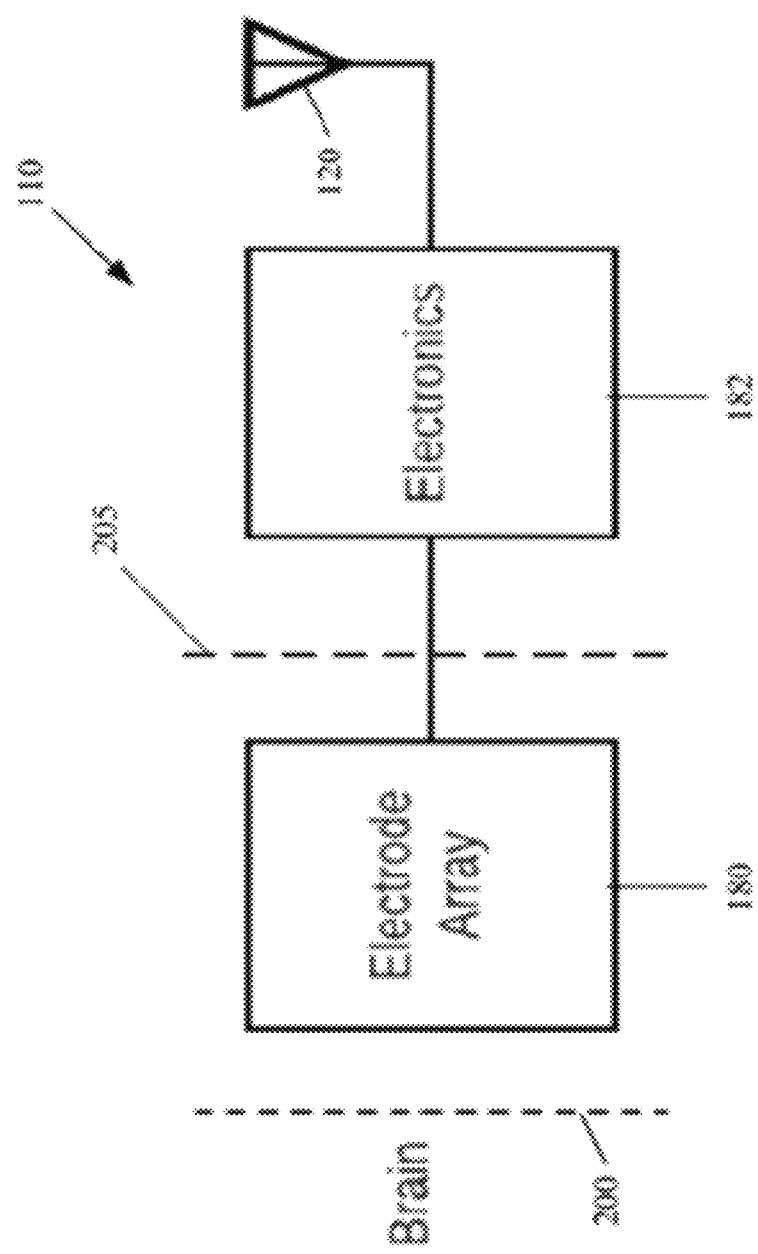
FIG. 2 depicts a diagram of a neural device, in accordance with an embodiment of the present disclosure.

In some embodiments, the neural device 110 described above can include a brain implant, such as is shown in FIG. 2. The neural device 110 may be a biomedical device configured to study, investigate, diagnose, treat, and/or augment brain activity. In some embodiments, components of the neural device 110 may be positioned between the brain 200 and the dura 205. The neural device 110 can include an electrode array 180 (which may be a component of or coupled to the electrode-amplifier stage 112 described above) that is configured to record and/or stimulate an area of the brain 200. The electrode array 180 can be connected to an electronics hub 182 (which can include one or more of the electrode-amplifier stage 112, analog front-end stage 114, ADC stage 116, and DSP stage 118) that is configured to transmit via wireless or wired transceiver 120 to the external device 130 (in some cases, referred to as a "receiver").

The electrode array 180 can include non-penetrating cortical surface microelectrodes (i.e., the electrode array 180 does not penetrate the brain 200). Accordingly, the neural device 110 can provide a high spatial resolution, with minimal invasiveness and improved signal quality. The minimal invasiveness of the electrode array 180 is beneficial because it allows the neural device 110 to be used with larger population of patients than conventional brain implants, thereby expanding the application of the neural device 110 and allowing more individuals to benefit from brain-computer interface technologies. Furthermore, the surgical procedures for implanting the neural devices 110 are minimally invasive, reversible, and avoid damaging neural tissue. In some embodiments, the electrode array 180 can be a high-density microelectrode array that provides smaller features and improved spatial resolution relative to conventional neural implants.

In some embodiments, the neural device 110 includes an electrode array configured to stimulate or record from neural tissue adjacent to the electrode array, and an integrated circuit in electrical communication with the electrode array, the integrated circuit having an analog-to-digital converter (ADC) producing digitized electrical signal output. In some embodiments, the ADC or other electronic components of the neural device 110 can include an encryption module, such as is described below. The neural device 110 can also include a wireless transmitter (e.g., the transceiver 120) communicatively coupled to the integrated circuit or the encryption module and an external device 130. The neural device 110 can also include, for example, control logic for operating the integrated circuit or electrode array 180, memory for storing recordings from the electrode array, and a power management unit for providing power to the integrated circuit or electrode array 180.

Figure 3:
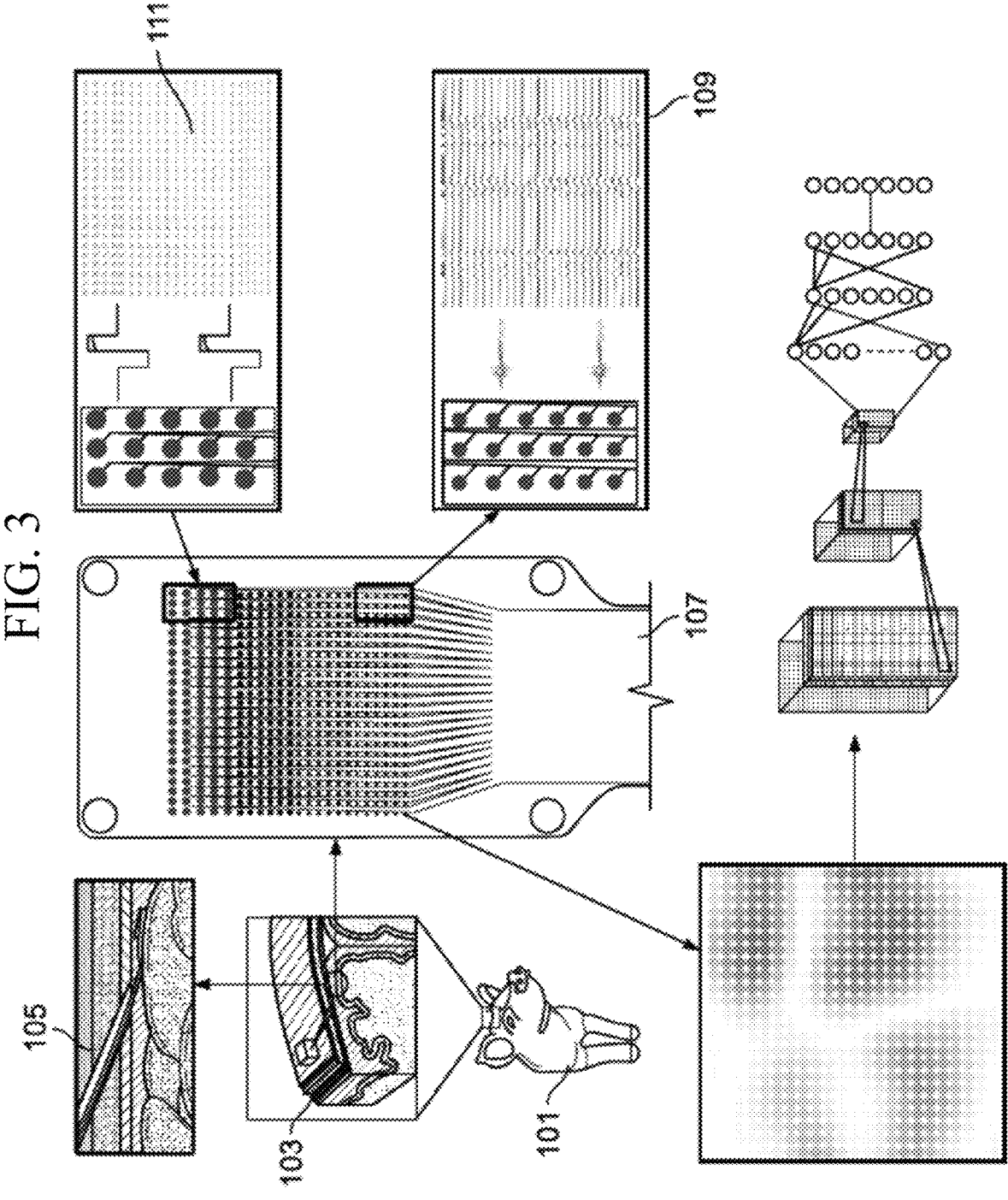
FIG. 3 depicts a diagram of a thin-film, microelectrode array neural device and implantation method, in accordance with an embodiment of the present disclosure.

Referring now to FIG. 3, there is shown a diagram of an illustrative embodiment of a neural device 110. In this embodiment, the neural device 110 includes an electrode array 180 including non-penetrating microelectrodes. As generally described above, the neural device 110 can be configured for minimally invasive subdural implantation using a cranial micro-slit implantation 105 (or via an alternative aperture such as a conventional burr hole or craniotomy) which places the thin-film microelectrode array 107 within the subdural 103 space of the animal brain, with electrodes in direct electrical contact with the cortical surface. In some embodiments, the animal 101 may undergo cranial micro-slit implantation 105 of a set of subdural micro-electrocorticography arrays including a total of over 2000 or more microelectrodes, in modules containing 529 or 1,024 channels each. A group of 200 micron microelectrodes and example stimulation waveform traces 111 and resulting post-stimulus activity is recorded over the entire array. A group of 20 micron microelectrodes were shown in detail with traces from recorded neural activity 109. As illustrated, the neural interface may be configured for neural recording and/or stimulation. For example, the neural interface may be configured to record spontaneous neural activity 111, as well as stimulus-evoked neural activity 109.

Further, the microelectrodes of the electrode array 180 can be arranged in a variety of different configurations and may vary in size. In this particular example, the electrode array 180 includes a first group 190 of electrodes (e.g., 200 μm microelectrodes) and a second group 192 of electrodes (e.g., 20 μm microelectrodes). Further, example stimulation waveforms in connection with the first group 190 of electrodes and the resulting post-stimulus activity recorded over the entire array is depicted for illustrative purposes. Still further, example traces from recorded neural activity recorded by the second group 192 of electrodes are likewise illustrated. In this example, the electrode array 180 provides multichannel data that can be used in a variety of electrophysiologic paradigms to perform neural recording of both spontaneous and stimulus-evoked neural activity, as well as decoding and focal stimulation of neural activity, across a variety of functional brain regions.

Additional information regarding brain-computer interfaces described herein can be found in Hettick et al, *The Layer 7 Cortical Interface: A Scalable and Minimally Invasive Brain-Computer Interface Platform*, bioRxiv 2022.01.02.474656; doi: https://doi.org/10.1101/2022.01.02.474656, which is hereby incorporated by reference herein in its entirety.

Real-Time Brain Activity Visualization

In order to enable real-time visualization of electrical activity at the cortical surface, the neural devices 110 described herein are configured to record and transmit electrocortical measurements with sufficient resolution such that changes in electrocortical activity can be visualized across different areas of the cortical surface, a sufficient sampling rate that allows for meaningful data to be extracted from highly time-varying brain electrical signal data, and sufficient latency such that the electrocortical measurements can be displayed with minimal time delay. The neural device 110 can include a number of different features that can enable the real-time visualization. These features could be embodied in hardware, software, or as physical features of the neural device 110 itself. For example, the spatial density of the electrode array 180 can be sufficiently high to capture high resolution electrocortical data. As another example, the latency of the neural device 110 can be sufficiently low such that the system is cable to acquire, compute, and render electrocortical data at a defined sampling rate with a minimal to not human-perceivable delay (i.e., in real-time). As another example, the electrode array 180 can include regularly or evenly spaced electrodes, which allows the neural interface system to precisely spatially correlate the sensed electrocortical signals with locations on the cortical surface and, thus, provides precise mapping of the areas of the brain. As yet another example, the electrode array 180 can be fabricated from a substantially transparent material that allows the cortical surface to be visualized with respect to the electrode array 180.

In real-time brain activity visualization, it would be desirable for the neural device 110 to be able to capture data across an entire area of interest along the cortical surface (e.g., a region of the cortical surface that corresponds to vision, speech, or somatosensory characteristics), rather than only a subset of the area of interest. Accordingly, the electrode array 180 of the neural device 110 can be of a sufficient size to measure one or more areas of interest along the cortical surface. In one embodiment, the neural device 110 can include a number of electrodes (i.e., channels) that is sufficient to measure one or more areas of the cortical surface of interest. For example, the electrode array 180 could include one thousand or more electrodes. In one illustrative embodiment, the electrode array 180 could include 1,024 electrodes.

Because of the temporal characteristics of brain signals, a neural device 110 configured for real-time brain activity visualization can sample each channel at a correspondingly high sample rate in order for meaningful real-time data to be extracted from the electrocortical activity. In some embodiments, the neural device 110 can be configured to sample each channel between from about 1 Hz to about 40 kHz. In one illustrative embodiment, the neural device 110 could be configured to record electrocortical measurements at up to about 30 kHz. In another illustrative embodiment, the neural device 110 could be configured to record electrocortical measurements at up to about 30 kHz.

In order to effectuate real-time brain activity visualization, it can be desirable for the electrode array 180 of the neural device 110 to be configured to record electrocortical activity at a high spatial resolution. Accordingly, the electrode array 180 of the neural device 110 can have electrodes that are sufficiently small and spaced at sufficiently small distances in order to define a high-density electrode array 180 that can, accordingly, capture high resolution electrocortical data. Such high-resolution data could be used to resolve electrographic features that could otherwise not be identified using lower resolution electrode arrays. In some embodiments, the electrodes of the electrode array 180 could be from about 10 μm to about 500 μm in width. In one illustrative embodiment, the electrodes of the electrode array 180 could be about 50 μm in width. In some embodiments, the electrodes of the electrode array 180 could be spaced by about 200 μm (i.e., 0.2 mm) to about 3,000 μm (i.e., 3 mm). In illustrative one embodiment, adjacent electrodes of the electrode array 180 could be spaced by about 400 μm. With a sufficiently high resolution, the neural device 110 could be used to visualize brain activity occurring at anywhere from the scale of the inter-electrode spacing to the centimeter scale (e.g., aging processes), which could allow the neural device 110 to be utilized in a variety of different applications for monitoring and studying different types of brain functions.

Because of the large number of data channels and the high rate at which each channel is sampled, the neural device 110 is capturing a voluminous amount of data at a rapid rate. Therefore, the neural device 110 can implement specialized systems and techniques to be able to process and display the voluminous electrocortical data in real-time. In one embodiment, the neural device 110 can implement various data compression algorithms in order to transmit the recorded electrocortical data (e.g., via the transceiver 120) with sufficiently minimal latency such that it can be visualized in real-time via an external device 130. In one embodiment, the hardware of the neural device 110 can be specifically fabricated to minimize latency in recording and transmitting the electrocortical data. For example, the neural device 110 can include a graphics processing unit (GPU) to provide GPU-accelerated or GPU-optimized computation. The GPU-accelerated or GPU-optimized computation can further be facilitated by the pattern in which the electrodes are spaced or arranged across the electrode array 180.

Figure 7A:
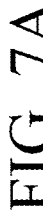
FIG. 7A depicts a closeup view of two neural device electrode array modules positioned over the cortical surface, in accordance with an embodiment of the present disclosure.
Figure 7B:
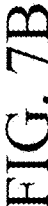
FIG. 7B depicts a view of a 1,024-electrode thin-film array in situ during human neurosurgery adjacent to a conventional 4-electrode "strip" array positioned over the cortical surface, in accordance with an embodiment of the present disclosure.

In one embodiment, the electrode array 180 can be constructed from a transparent or substantially transparent substrate. This embodiment could be beneficial because it would allow for the underlying cortical surface to be visualized with respect to the electrode array 180. For example, FIGS. 7A and 7B depict a pair of electrode array modules fabricated from such a substantially transparent material positioned against the cortical surface.

In one illustrative embodiment, the neural device 110 can include chips and controllers made by Intan Technologies (Los Angeles, California, United States of America). The custom amplifier printed circuit boards (PCBs) used to interface with the implanted electrode arrays each contained eight of the RHD2164 64-channel amplifier chips and one of the RHS2116 16-channel stimulator/amplifier chips, allowing for simultaneous recording from up to 528 channels and stimulation from up to 16 channels. In addition, each board allows for a hardware reference from one of 16 sites distributed across the array. The digitized data is transferred from the amplifier boards to an associated Intan Technologies 1,024-channel RHD controller or 126-channel RHS controller using low-voltage differential signaling (LVDS). The external devices 130 can interface with either controller via a custom configuration of the Intan Technologies RHX Data Acquisition Software, which allows for real-time event-triggered averaging in addition to base functionality. In one illustrative implementation, the sampling rate for recording via the neural device 110 was set at 30 kHz per channel, generating data at a rate over 2.5 GB per minute for each set of 1,024 channels. A 60 Hz notch filter is applied online during recording. For post-hoc analysis of local field potentials, data can be downsampled to 5 kHz using a Fourier method, then processed with a 5th-order Butterworth low-pass filter at 250 Hz.

Examples—Neural Recording

Figure 4A:
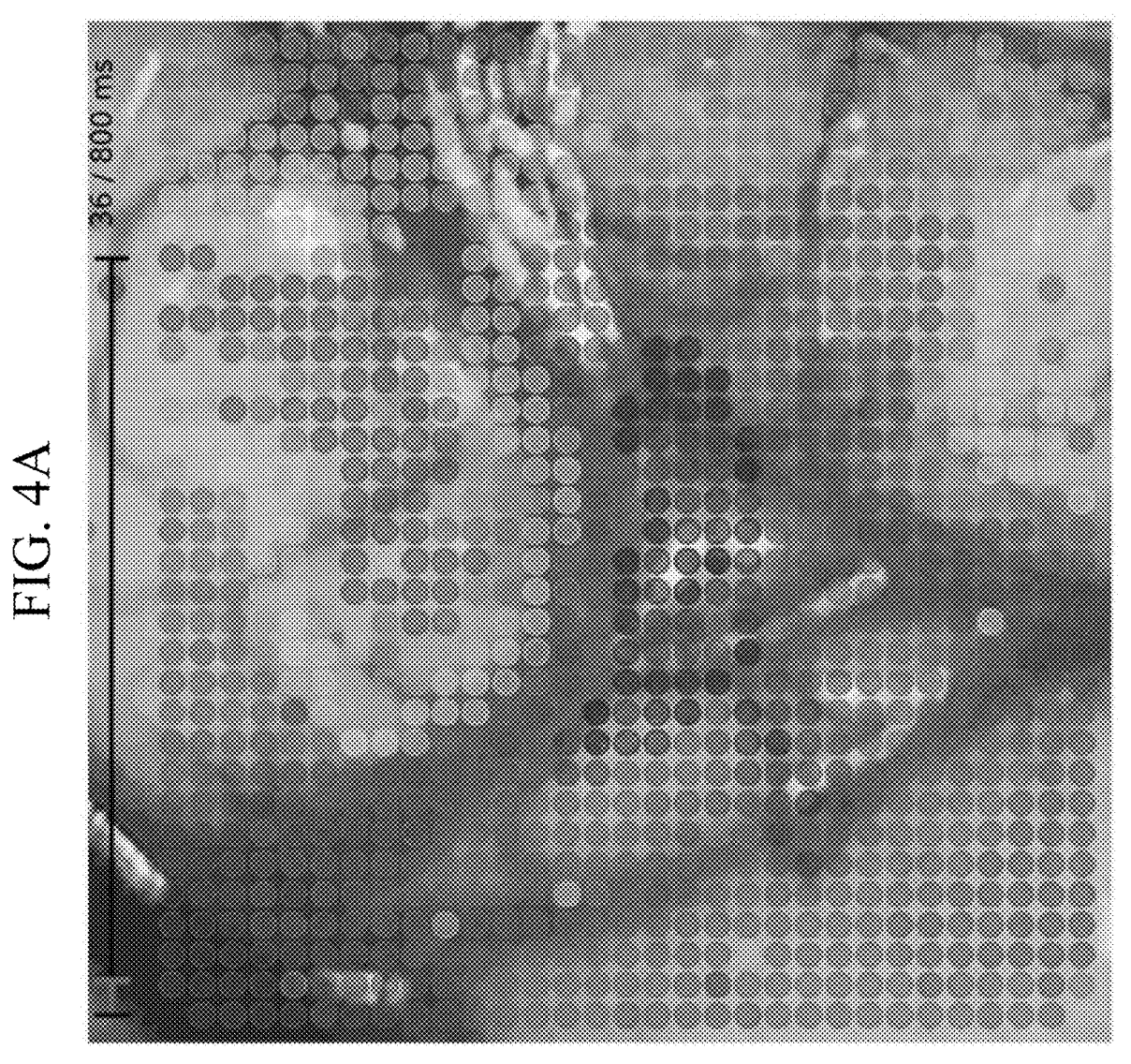
Figure 4B:
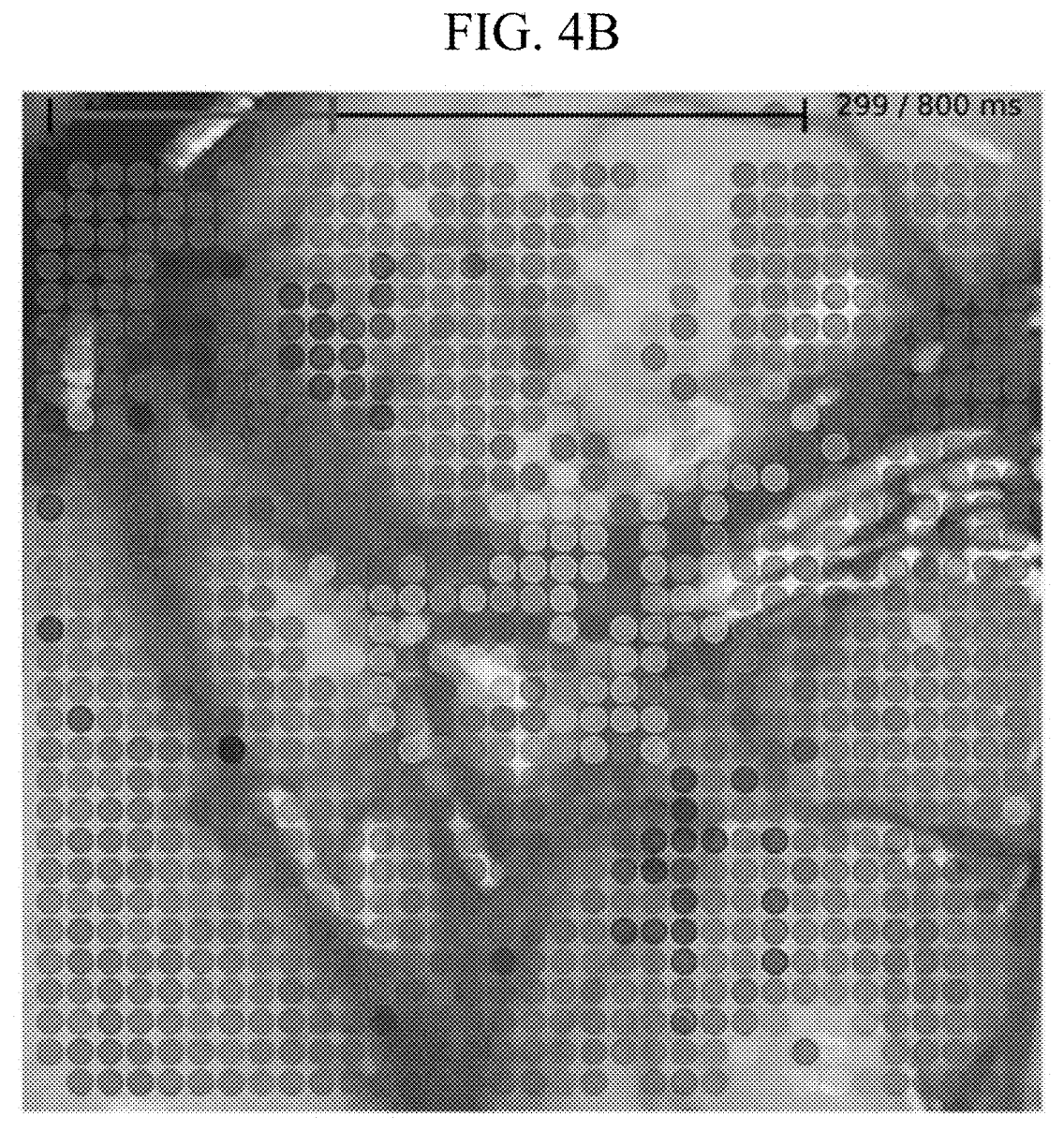
Figure 4C:
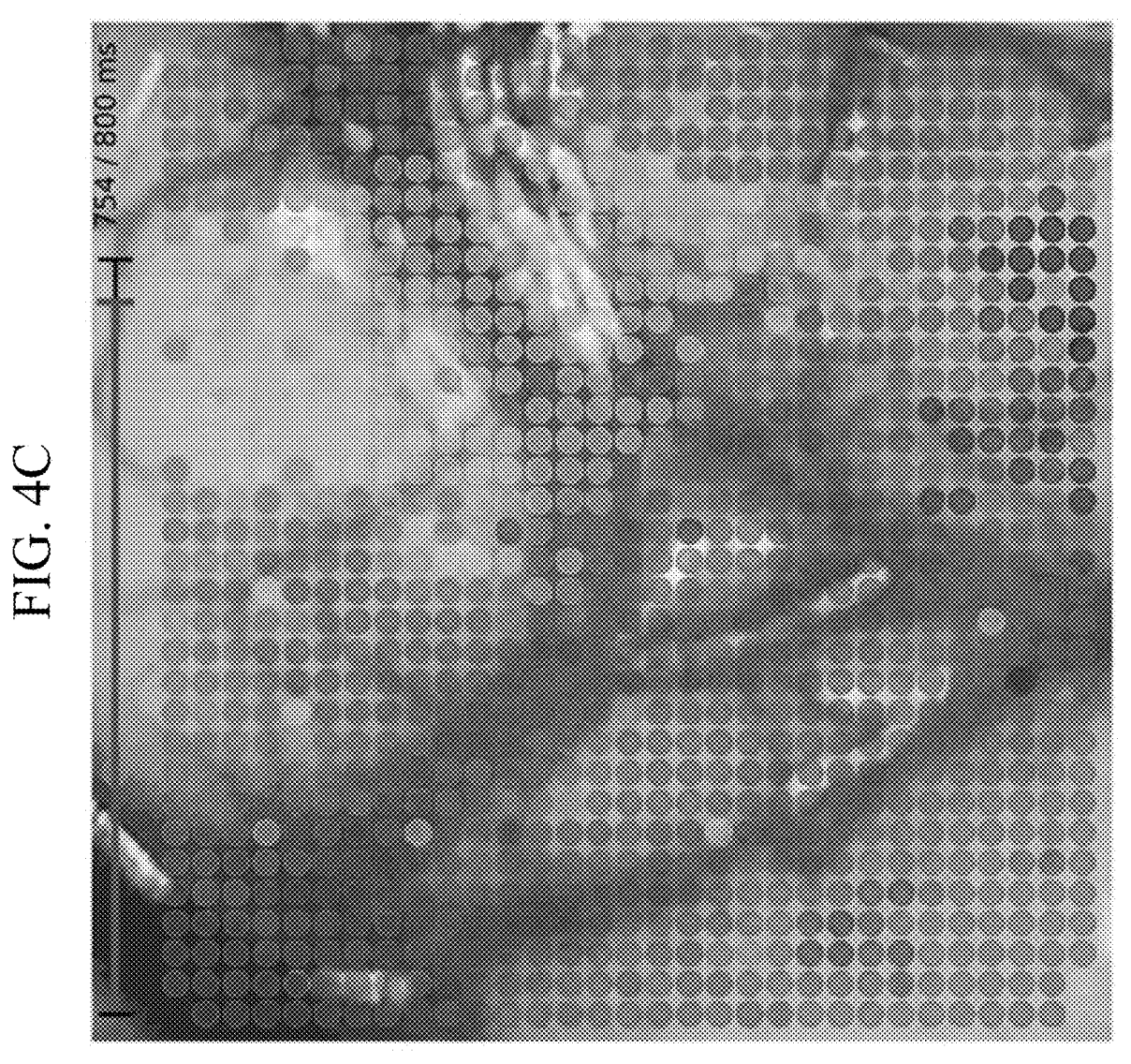
Figure 4D:
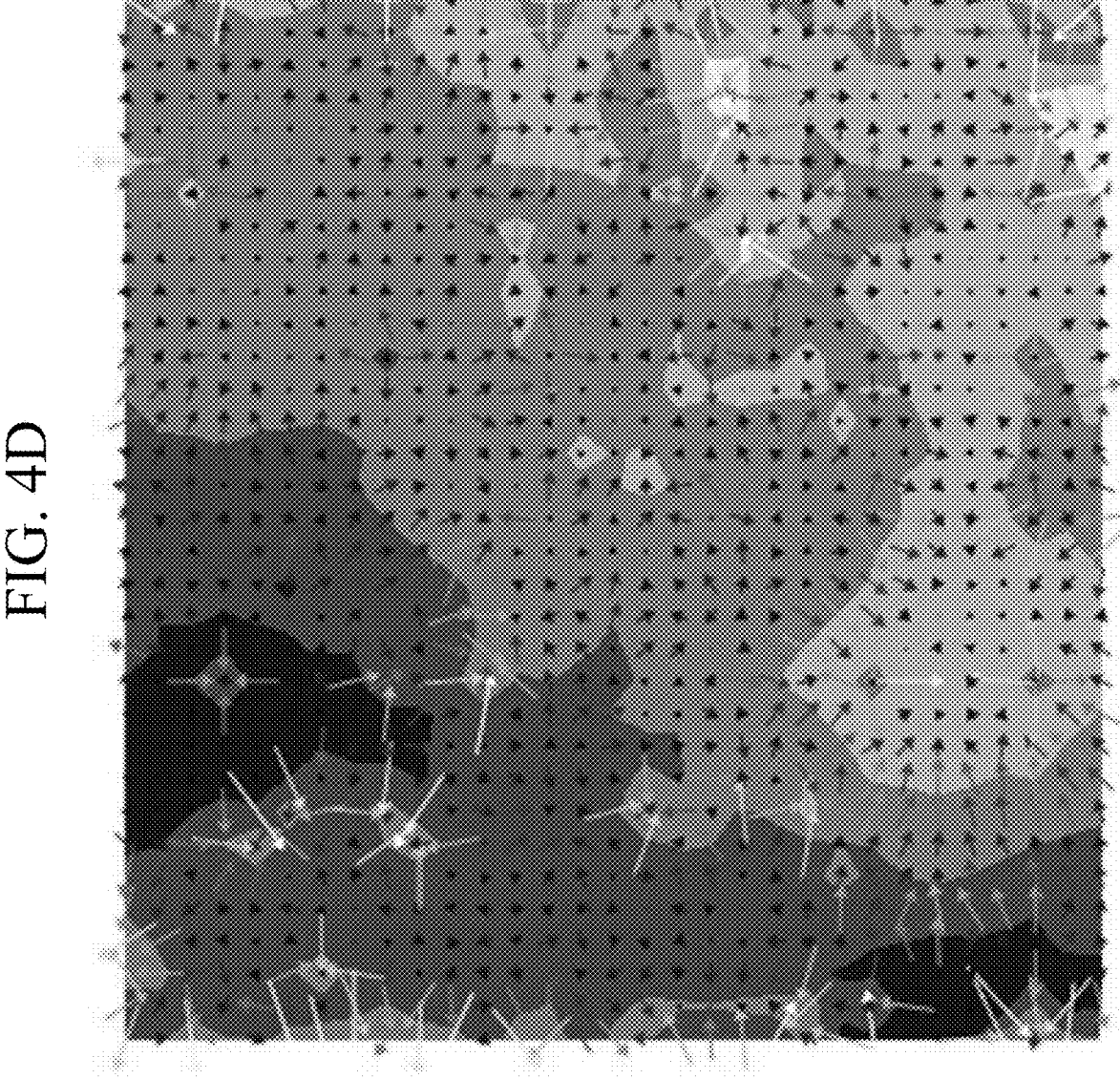
FIG. 4D depicts an example real-time visualization of first spatial derivatives of cortical surface voltage, in accordance with an embodiment of the present disclosure.
Figure 5:
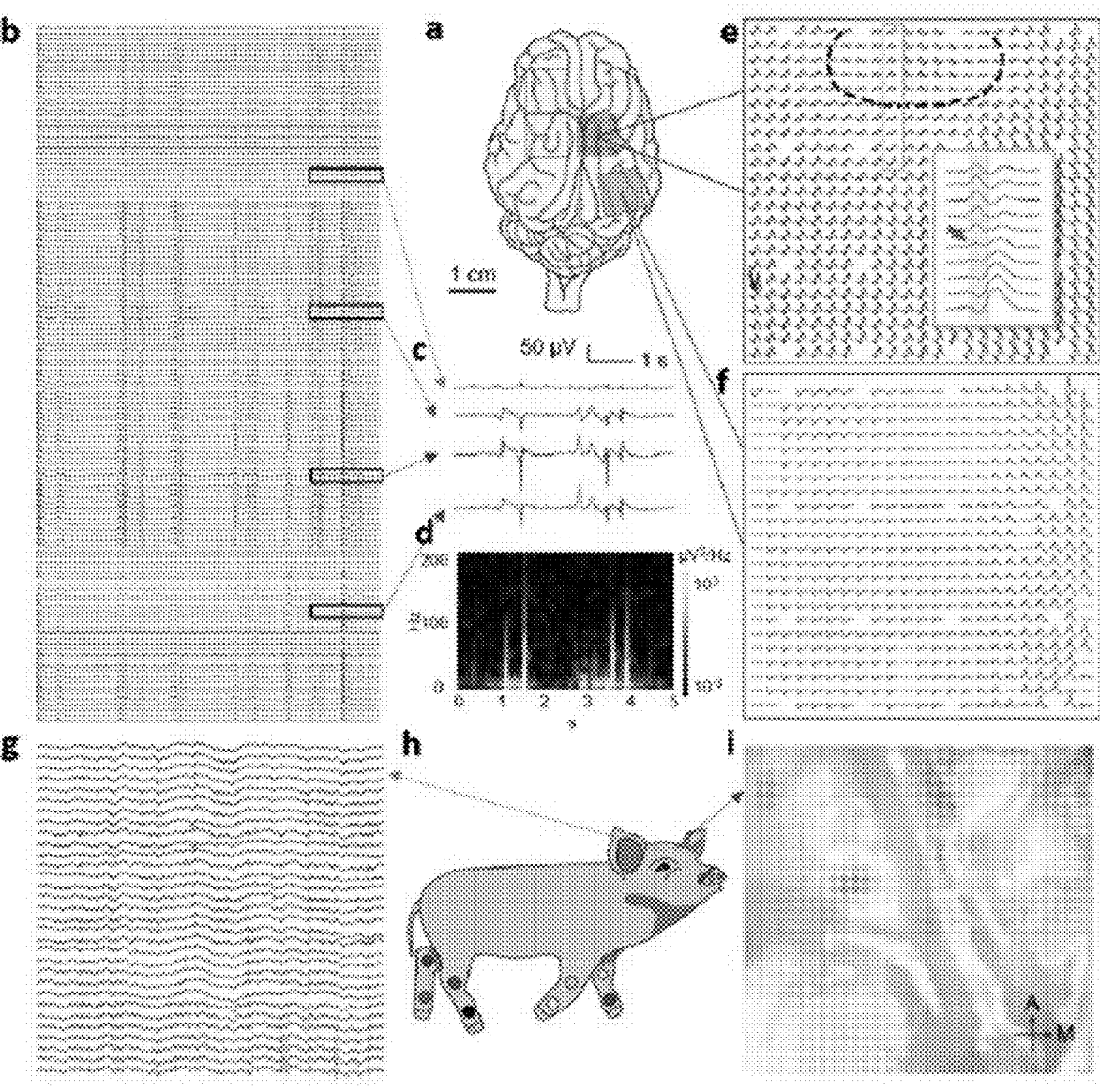
FIG. 5 depicts data from neural recording in Göttingen minipigs, in accordance with an embodiment of the present disclosure.

As discussed above, the neural devices 110 can provide high resolution and data bandwidth to map electrocortical activity on a fine-grained scale. In preclinical studies involving Göttingen minipigs, implanted arrays were used for high-bandwidth and high-spatial resolution neural recording of both spontaneous cortical electrographic activity and evoked potentials from multiple functional regions. During free recording of spontaneous cortical activity, the software of the system 100 was able to enable real-time visualization of both raw voltages and spectral power across more than 1,000 channels simultaneously. One illustrative visualization from the software overlaid on the cortical surface of the subject is shown in FIGS. 4A-C, for reference. In addition to system 100 displaying raw electrocortical measurements (e.g., voltages and spectral power), the system 100 can also visualize derivatives of the electrocortical measurements or other parameters derived from the measured data. For example, another illustrative visualization from the software is shown in FIG. 4D. The example shown in FIG. 4D depicts a visualization of real-time first spatial derivatives of the cortical surface voltage captured via a 1,024-electrode thin-film electrode array 180. In other embodiments, the system 100 can generate visualization by applying causal or acausal image- or video-filtering techniques to the recorded electrocortical data. As can be seen, the cortical electrographic activity sensed via the neural device electrode array is highly dynamic. Further, the neural device electrode array is able to provide a high resolution, real-time visualization of the cortical electrographic activity. As shown in FIG. 5, recorded electrocortical activity from individual channels can be viewed in both time and frequency domains, revealing the presence of electrocortical activity at frequencies up to 500 Hz. The degree of correlation across electrodes decreases with distance and with increasing frequency. Importantly, even at 400 μm spacing, adjacent electrodes exhibit incompletely correlated activity, particularly at higher frequencies. For example, beta-band $r^2$ is in the range of 0.45±0.03 at 400 μm spacing for 50 μm electrodes, suggesting that even at this spatial scale the total amount of electrophysiologic information available at the cortical surface has not been completely extracted.

To further explore the utility of high-spatial density neural recording, evoked potentials were obtained across multiple arrays and multiple functional regions. Robust somatosensory evoked potentials (SSEPs) were obtained in arrays positioned over the somatosensory cortex following electrical or tactile stimulation of all four of the limbs. When the arrays span both motor and sensory cortex, the SSEPs demonstrate clear phase reversal at the motor-sensory junction; in contrast to traditional macroelectrode strips, which enable only coarse localization of the boundary to within multiple millimeters, we are able to identify this boundary as an isoelectric contour line with 300 μm resolution, providing precise mapping of functional boundaries on the cortical surface. Robust visual evoked potentials (VEPs) were similarly obtained in arrays positioned over the visual cortex following time-synchronized photostimulation of the retina (f, FIG. 5). We also recorded electrocorticographic activity in awake, freely ambulating animals (g and h, FIG. 5). Time-synchronized neural data from 2,048 channels (i.e., 1,024 channels per hemisphere in the region of primary sensorimotor cortex) was acquired together with three-dimensional motion capture data using multiple fiducial markers on each limb (h, FIG. 5), as well as accelerometers mounted on all four limbs and the head.

Examples—Human Intraoperative Electrocorticography

In a pilot clinical study involving neurosurgical patients undergoing intraoperative electrophysiologic mapping, the ability of the system 100 to acquire, process, and display high-spatiotemporal-resolution electrocortical data in real time was further evaluated. Spontaneous electrocortical recordings were obtained in patients under general anesthesia, on conventional four-electrode strips and in higher resolution on the 1,024-electrode devices. Multiple patients underwent awake language mapping and 1,024-channel electrocortical recordings were obtained, time-synchronized to auditory or single-word visual cues, as shown in FIG. 6 for an example patient with a tumor in the left superior temporal gyrus and angular gyrus.

Figure 6:
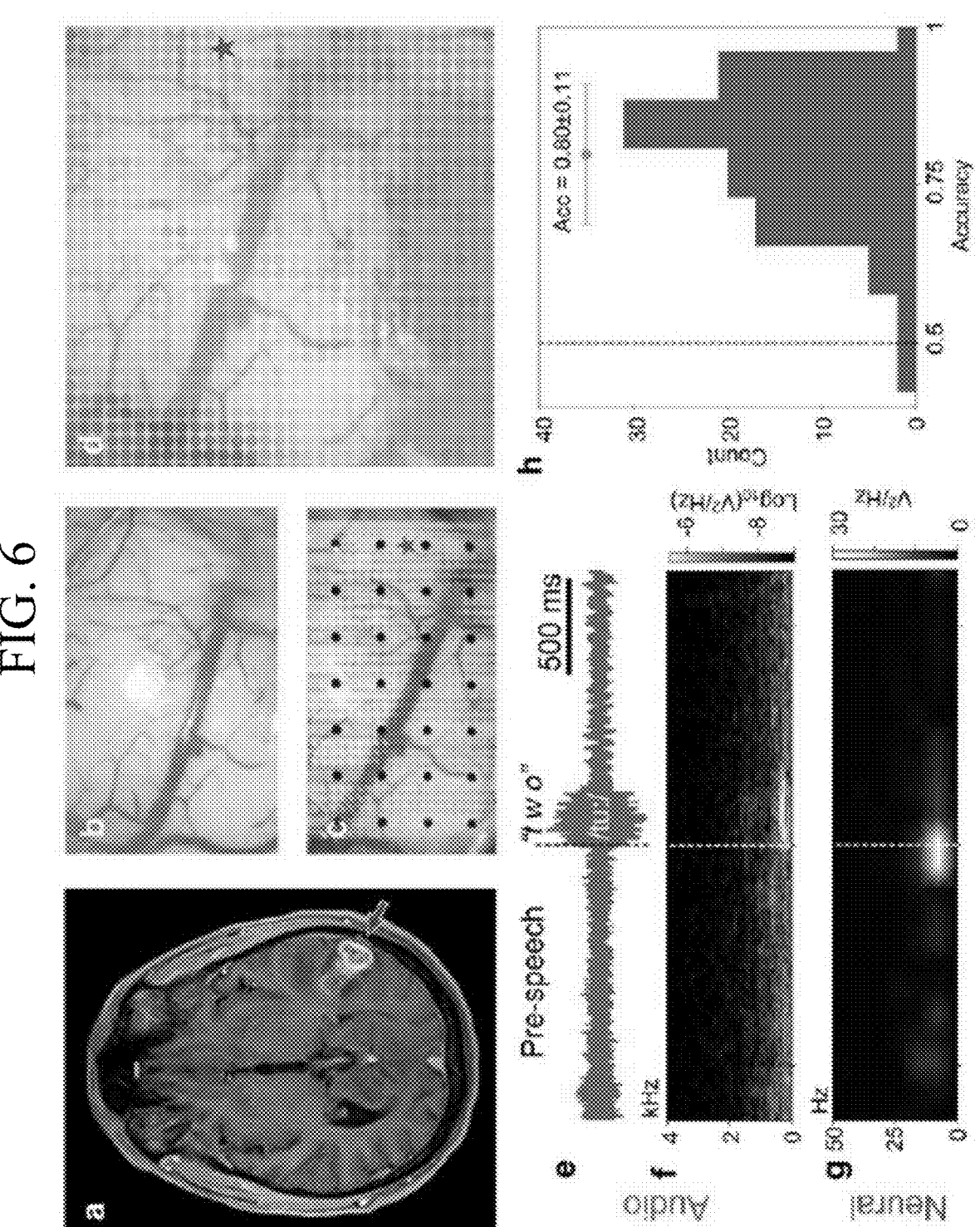
FIG. 6 depicts data from human intraoperative electrocorticography, in accordance with an embodiment of the present disclosure.

Referring to FIG. 6 in further detail, axial gadolinium-contrast-enhanced T1-weighted MRI of the brain of one patient involved in the pilot study, demonstrating a tumor in the left temporal lobe (a, FIG. 6). The arrow indicates placement of a 1,024-channel electrode array during awake language mapping. Cortical surface of the left superior temporal gyrus prior to (b, FIG. 6) and following (c, FIG. 6) electrode array placement are additionally shown. FIG. 6 further depicts an overlay-representation of electrocortical activity (d, FIG. 6) from the 1,024-channel electrode array at the time point indicated by the dashed line in (e and f, FIG. 6), immediately prior to speech onset. The map represents normalized raw voltage as obtained from the digital steps of the analog-to-digital converter (darker representing lower voltages and lighter representing higher voltages). FIG. 6 further depicts audio amplitude recorded during patient speech (e, FIG. 6) relative to a time-frequency spectrogram of audio recording during the same time interval (f, FIG. 6) and a time-frequency spectrogram of the voltage waveform from a representative electrode (g, FIG. 6). Finally, FIG. 6 further includes a bar graph demonstrating the accuracy of decoding speech onset on the basis of a 4-minute training set of spoken words, in offline decoding, as assessed in 100 randomly shuffled train-test samples (h, FIG. 6).

This disclosure is not limited to the particular systems, devices, and methods described, as these may vary. The terminology used in the description is for the purpose of describing the particular versions or embodiments only and is not intended to limit the scope of the disclosure.

The following terms shall have, for the purposes of this application, the respective meanings set forth below. Unless otherwise defined, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention.

As used herein, the term "real-time" means a latency that is sufficiently low such that a human does not perceive a delay or perceives only a minimal delay between the occurrence of an event (e.g., electrocortical data) and the rendering of the event by the system. In some embodiments, real-time could include a latency of less than 200 ms. In other embodiments, real-time could include a latency of less than 100 ms.

As used herein, the singular forms "a," "an," and "the" include plural references, unless the context clearly dictates otherwise. Thus, for example, reference to a "protein" is a reference to one or more proteins and equivalents thereof known to those skilled in the art, and so forth.

As used herein, the term "about" means plus or minus 10% of the numerical value of the number with which it is being used. Therefore, about 50 mm means in the range of 45 mm to 55 mm.

As used herein, the term "consists of" or "consisting of" means that the device or method includes only the elements, steps, or ingredients specifically recited in the particular claimed embodiment or claim.

In embodiments or claims where the term "comprising" is used as the transition phrase, such embodiments can also be envisioned with replacement of the term "comprising" with the terms "consisting of" or "consisting essentially of."

As used herein, the term "subject" includes, but is not limited to, humans and non-human vertebrates such as wild, domestic, and farm animals.

While the present disclosure has been illustrated by the description of exemplary embodiments thereof, and while the embodiments have been described in certain detail, it is not the intention of the Applicants to restrict or in any way limit the scope of the appended claims to such detail. Additional advantages and modifications will readily appear to those skilled in the art. Therefore, the disclosure in its broader aspects is not limited to any of the specific details, representative devices and methods, and/or illustrative examples shown and described. Accordingly, departures may be made from such details without departing from the spirit or scope of the Applicant's general inventive concept.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

In addition, even if a specific number is explicitly recited, those skilled in the art will recognize that such recitation should be interpreted to mean at least the recited number (for example, the bare recitation of "two recitations," without other modifiers, means at least two recitations, or two or more recitations). Furthermore, in those instances where a convention analogous to "at least one of A, B, and C, et cetera" is used, in general such a construction is intended in the sense one having skill in the art would understand the convention (for example, "a system having at least one of A, B, and C" would include but not be limited to systems that have A alone, B alone, C alone, A and B together, A and C together, B and C together, and/or A, B, and C together, et cetera). In those instances where a convention analogous to "at least one of A, B, or C, et cetera" is used, in general such a construction is intended in the sense one having skill in the art would understand the convention (for example, "a system having at least one of A, B, or C" would include but not be limited to systems that have A alone, B alone, C alone, A and B together, A and C together, B and C together, and/or A, B, and C together, et cetera). It will be further understood by those within the art that virtually any disjunctive word and/or phrase presenting two or more alternative terms, whether in the description, sample embodiments, or drawings, should be understood to contemplate the possibilities of including one of the terms, either of the terms, or both terms. For example, the phrase "A or B" will be understood to include the possibilities of "A" or "B" or "A and B."

In addition, where features of the disclosure are described in terms of Markush groups, those skilled in the art will recognize that the disclosure is also thereby described in terms of any individual member or subgroup of members of the Markush group.

Various of the above-disclosed and other features and functions, or alternatives thereof, may be combined into many other different systems or applications. Various presently unforeseen or unanticipated alternatives, modifications, variations or improvements therein may be subsequently made by those skilled in the art, each of which is also intended to be encompassed by the disclosed embodiments.

The invention claimed is:

1. A neural device for real-time visualization of neural activity at a cortical surface of a patient, the neural device comprising:
   an electrode array comprising:
      a substantially transparent film substrate with a thickness of about 50 micrometers; and
      a plurality of electrodes disposed on the substantially transparent film substrate, wherein the plurality of electrodes number at least about 500;
   wherein the electrode array records at a frequency from about 1 Hz to about 40 kHz;
   wherein a width of each of the plurality of electrodes is from about 10 μm to about 500 μm;
   wherein each of the plurality of electrodes is spaced from an adjacent electrode of the plurality of electrodes from about 200 μm to about 3,000 μm;
   a transceiver coupled to the electrode array, the transceiver configured to transmit electrocortical data captured via the electrode array to an external device with a latency less than about 200 ms; and
   a graphics processing unit (GPU) coupled to the electrode array and the transceiver, the GPU configured to process the electrocortical data via GPU-accelerated or GPU-optimized computation to minimize the latency of recording and transmitting the electrocortical data.

2. The neural device of claim 1, wherein the plurality of electrodes comprise electrodes that do not penetrate the cortical surface.

3. The neural device of claim 1, wherein:
   the neural device is communicably coupled to an external device via the transceiver; and
   the electrocortical data can be visualized on the external device in real-time.

4. The neural device of claim 1, wherein the plurality of electrodes number an integer multiple of 1,024.

5. The neural device of claim 1, wherein the electrode array comprises a thin-film electrode array.

6. The neural device of claim 1, wherein the neural device comprises a flexible substrate on which the electrode array is disposed.

7. The neural device of claim 1, wherein the plurality of electrodes are spaced regularly.

8. A neural interface system for real-time visualization of a cortical surface of a patient, the neural interface system comprising:

a neural device comprising:

an electrode array comprising:

a substantially transparent film substrate with a thickness of about 50 micrometers; and a plurality of electrodes disposed on the substantially transparent film substrate, wherein the plurality of electrodes number at least about 500, wherein the electrode array records at a frequency of up to about 30 kHz, wherein a width of each of the plurality of electrodes is from about 5 μm to about 100 μm, wherein each of the plurality of electrodes is spaced from an adjacent electrode of the plurality of electrodes by less than about 400 μm, a transceiver coupled to the electrode array, the transceiver configured to transmit electrocortical data captured via the electrode array to an external device with a latency less than about 200 ms, and a graphics processing unit (GPU) coupled to the electrode array and the transceiver, the GPU configured to process the electrocortical data via GPU-accelerated or GPU-optimized computation to minimize the latency of recording and transmitting the electrocortical data; and the external device communicably coupled to the neural device via the transceiver, the external device comprising a processor and a memory, the memory storing instructions that, when executed by the processor cause the external device to:

14 receive the electrocortical data from the neural device, and render neural activity corresponding to the received electrocortical data in real-time in correspondence with an anatomy of the cortical surface underlying the electrode array.

9. The neural interface system of claim 8, wherein a rendering of the neural activity comprises at least one of spark-lines or colorized representations of (a) voltage or spectral power associated with each of the plurality of electrodes, (b) spatial or temporal derivatives of the voltage or the spectral power across the electrode array, or (c) causal or acausal image- or video-filtering techniques applied to the received electrocortical data.

10. The neural interface system of claim 8, wherein the plurality of electrodes comprise electrodes that do not penetrate the cortical surface.

11. The neural interface system of claim 8, wherein:

the neural device is communicably coupled to the external device via the transceiver; and the electrocortical data can be visualized on the external device in real-time.

12. The neural interface system of claim 8, wherein the plurality of electrodes number an integer multiple of 1,024.

13. The neural interface system of claim 8, wherein electrode array comprises a thin-film electrode array.

14. The neural interface system of claim 8, wherein the neural device comprises a flexible substrate on which the electrode array is disposed.

15. The neural interface system of claim 8, wherein the plurality of electrodes are spaced regularly.

* * * * *